US012791509B2

(12) United States Patent
Sugiyama et al.

(10) Patent No.: US 12,791,509 B2
(45) Date of Patent: Nov. 10, 2026

(54) GAS DETECTION METHOD, INFORMATION PROCESSING APPARATUS, METHOD OF DIAGNOSING A PLANT, AND PLANT DIAGNOSING APPARATUS

(71) Applicant: Sony Group Corporation, Tokyo (JP)

(72) Inventors: Taiki Sugiyama, Tokyo (JP); Michiko Nakao, Tokyo (JP); Ryota Yamano, Tokyo (JP); Yuichi Ishida, Tokyo (JP)

(73) Assignee: Sony Group Corporation, Tokyo (JP)

( * ) Notice: Subject to any disclaimer, the term of this patent is extended or adjusted under 35 U.S.C. 154(b) by 307 days.

(21) Appl. No.: 18/285,774

(22) PCT Filed: Feb. 28, 2022

(86) PCT No.: PCT/JP2022/008215
§ 371 (c)(1),
(2) Date: Oct. 5, 2023

(87) PCT Pub. No.: WO2022/219945
PCT Pub. Date: Oct. 20, 2022

(65) Prior Publication Data
US 2024/0192158 A1 Jun. 13, 2024

(30) Foreign Application Priority Data
Apr. 13, 2021 (JP) ................................ 2021-067823

(51) Int. Cl.
*G01N 27/12* (2006.01)
*G01N 33/00* (2006.01)
(Continued)

(52) U.S. Cl.
CPC ....... *G01N 27/125* (2013.01); *G01N 33/0027* (2013.01); *G01N 33/0098* (2013.01);
(Continued)

(58) Field of Classification Search
CPC .......... G01N 33/4977; G01N 33/4975; G01N 33/0098; G01N 33/0027; G01N 27/125; A01G 7/00
See application file for complete search history.

(56) References Cited

U.S. PATENT DOCUMENTS 4,414,839 A * 11/1983 Dilley ................. G01N 33/025 73/31.06
10,294,099 B1 * 5/2019 Biaggi-Labiosa ... G01N 33/004
(Continued)

FOREIGN PATENT DOCUMENTS

CN 106908488 A 6/2017
JP H11304746 A 11/1999
(Continued)

OTHER PUBLICATIONS

Qiuni Zhao, Zaihua Duan, Zhen Yuan, Xian Li, Si Wang, Bohao Liu, Yajie Zhang, Yadong Jiang, Huiling Tai. High performance ethylene sensor based on palladium-loaded tin oxide: Application in fruit quality detection[J]. Chin. Chem. Lett., 2020, 31(8): 2045-2049.*
(Continued)

*Primary Examiner* — Nathaniel J Kolb
(74) *Attorney, Agent, or Firm* — K&L Gates LLP

(57) ABSTRACT

[Object] To provide a gas detection method, an information processing apparatus, a method of diagnosing a plant, and a plant diagnosing apparatus that are capable of easily identifying a specific gas species.
[Solving Means] A gas detection method according to an embodiment of the present technology includes: heating a semiconductor sensor that includes an adsorption layer formed of a metal oxide; measuring a resistance value of the semiconductor sensor in an air atmosphere in which a reducing gas is present; and determining, where the measured resistance value is high in a first temperature range and low in a second temperature range higher than the first
(Continued)

temperature range with reference to the resistance value of the semiconductor sensor in an air atmosphere in which the reducing gas is not present, that the reducing gas contains a hydrocarbon substance emitted from a plant or an animal.

18 Claims, 16 Drawing Sheets

(51) Int. Cl.
*G01N 33/497* (2006.01)
*A01G 7/00* (2006.01)

(52) U.S. Cl.
CPC ........... *G01N 33/4975* (2024.05); *A01G 7/00* (2013.01); *G01N 33/4977* (2024.05)

(56) References Cited

U.S. PATENT DOCUMENTS

| | | | | |
|---|---|---|---|---|
| 2017/0363556 | A1 | 12/2017 | Nagase et al. | |
| 2020/0116694 | A1 * | 4/2020 | Rinaldi ................ | G01N 27/125 |
| 2022/0412910 | A1 | 12/2022 | Sugiyama et al. | |

FOREIGN PATENT DOCUMENTS

| | | | | |
|---|---|---|---|---|
| JP | 2001175969 | A | | 6/2001 |
| JP | 2005043291 | A | * | 2/2005 |
| JP | 2005134311 | A | | 5/2005 |
| JP | 2016065868 | A | | 4/2016 |
| JP | 2017223557 | A | | 12/2017 |
| KR | 20210004484 | A | | 1/2021 |
| WO | 2021106615 | A1 | | 6/2021 |

OTHER PUBLICATIONS

Paczkowski, S.; Datta, P.; Irion, H.; Paczkowska, M.; Habert, T.; Pelz, S.; Jaeger, D. Evaluation of Early Bark Beetle Infestation Localization by Drone-Based Monoterpene Detection. Forests 2021, 12, 228. https:/ /doi.org/10.3390/f12020228.*

Qiuni Zhao, Zaihua Duan, Zhen Yuan, Xian Li, Si Wang, Bohao Liu, Yajie Zhang, Yadong Jiang, Huiling Tai. High performance ethylene sensor based on palladium-loaded tin oxide: Application in fruit quality detection[J]. Chin. Chem. Lett., 2020, 31(8): 2045-2049. (Year: 2020).*

Paczkowski, S.; Datta, P.; Irion, H.; Paczkowska, M.; Habert, T.; Pelz, S.; Jaeger, D. Evaluation of Early Bark Beetle Infestation Localization by Drone-Based Monoterpene Detection. Forests 2021, 12, 228. https:/ /doi.org/10.3390/f12020228. (Year: 2021).*

Machine translation of JP 2005043291 (Year: 2005).*

Zhao et al: "High performance ethylene sensor based on palladium-loaded tin oxide: Application in fruit quality detection", Chinese Chemical Letters, Elsevier, Amsterdam, NL, vol. 31, No. 8, May 1, 2020, pp. 2045-2049, XP086224736, ISSN: 1001-8417, DOI: 10.1016/J.CCLET.2020.04.032 [retrieved on May 1, 2020] * the whole document *.

International Search Report from corresponding PCT application PCT/JP2022/008215, dated May 17, 2022.

Paczkowski, Sebastian et al.; "Evaluation of Early Bark Beetle Infestation Localization by Drone-based Monoterpene Detection"; Forests, Feb. 16, 2021, vol. 12, 228, <URL : https ://doi. org/10. 3390/f12020228>.

Matsui, Kenji; "松井健二 みどりの香り研究の 最前線 香料,"; Frontier of study on green leaf volatiles, The koryo. No. 244, Dec. 2009, pp. 21-34.

* cited by examiner

GAS DETECTION METHOD, INFORMATION PROCESSING APPARATUS, METHOD OF DIAGNOSING A PLANT, AND PLANT DIAGNOSING APPARATUS

TECHNICAL FIELD

The present technology relates to a gas detection method, an information processing apparatus, a method of diagnosing a plant, and a plant diagnosing apparatus.

BACKGROUND ART

A technology for using a metal oxide (MOx) semiconductor sensor to detect and identify a gas has been known. For example, Patent Literature 1 discloses a gas sensor that includes an adsorption layer and a sensing layer, the adsorption layer adsorbing a gas containing a detection target gas and a non-detection target gas, the sensing layer being covered with the adsorption layer, electrical properties of the sensing layer changing depending on the concentration of the detection target gas that has passed through the adsorption layer. Further, Patent Literature 2 disclose a gas detection apparatus that identifies the type of gas on the basis of the output values of a first gas sensor and a second gas sensor.

CITATION LIST

Patent Literature

Patent Literature 1: Japanese Patent Application Laid-open No. 2017-223557

Patent Literature 2: Japanese Patent Application Laid-open No. 2001-175969

DISCLOSURE OF INVENTION

Technical Problem

When a reducing gas is sprayed while heating a MOx semiconductor sensor, the resistance value of the semiconductor sensor generally starts to change from a certain temperature. In this regard, a gas can be detected or quantified from the amount of change (sensitivity) in the resistance value. Further, when there is a large difference in profiles of the amount of change (sensitivity) in the temperature and resistance, the type of gas can be identified. However, in the case where there is no sufficient difference in the profiles, it has been difficult to identify the type of gas.

In view of the circumstances as described above, it is an object of the present technology to provide a gas detection method, an information processing apparatus, a method of diagnosing a plant, and a plant diagnosing apparatus that are capable of easily identifying a specific gas species.

Solution to Problem

A gas detection method according to an embodiment of the present technology includes: heating a semiconductor sensor that includes an adsorption layer formed of a metal oxide.

A resistance value of the semiconductor sensor in an air atmosphere in which a reducing gas is present is measured.

It is determined, where the measured resistance value is high in a first temperature range and low in a second temperature range higher than the first temperature range with reference to the resistance value of the semiconductor sensor in an air atmosphere in which the reducing gas is not present, that the reducing gas contains a hydrocarbon substance emitted from a plant or an animal.

The air atmosphere in which the reducing gas is not present may be dry air.

The semiconductor sensor may include a plurality of semiconductor sensors. In this case, the step of heating the semiconductor sensor includes heating each of the plurality of semiconductor sensors to different heating temperatures, and the step of measuring a resistance value of the semiconductor sensor includes measuring a resistance value of each of the plurality of semiconductor sensors.

The hydrocarbon substance may be a substance containing a C6 linear aliphatic compound.

The hydrocarbon substance may have a molecular weight of 90 or more and 160 or less.

The metal oxide may be a sintered body containing a metal oxide material and a catalyst metal material.

The metal oxide material may include a tungsten oxide, an indium oxide, a tin oxide, or a zinc oxide, and the catalyst metal material may include iridium, an oxide thereof, palladium, an oxide thereof, rhenium, or an oxide thereof.

A gas detection method according to another embodiment of the present technology includes: heating a semiconductor sensor that includes an adsorption layer formed of a metal oxide.

A resistance value of the semiconductor sensor in an air atmosphere in which a reducing gas is present is measured.

It is determined, where sensitivity that is a ratio of a resistance value the semiconductor sensor in the air atmosphere in which the reducing gas is not present to the measured resistance value is less than one in a first temperature range and greater than one in a second temperature range higher than the first temperature range, that the reducing gas contains a hydrocarbon substance emitted from a plant or an animal.

An information processing apparatus according to an embodiment of the present technology includes: an acquisition unit; and a determination unit.

The acquisition unit acquires a resistance value of a metal oxide semiconductor sensor in an air atmosphere in which a reducing gas is present.

The determination unit determines, where the acquired resistance value is high in a first temperature range and low in a second temperature range higher than the first temperature range with reference to the resistance value of the semiconductor sensor in an air atmosphere in which the reducing gas is not present, that the reducing gas contains a hydrocarbon substance emitted from a plant or an animal.

An information processing apparatus according to another embodiment of the present technology includes: an acquisition unit; and a determination unit.

The acquisition unit acquires a resistance value of a metal oxide semiconductor sensor in an air atmosphere in which a reducing gas is present.

The determination unit determines, where sensitivity that is a ratio of a resistance value of the semiconductor sensor in the air atmosphere in which the reducing gas is not present to the acquired resistance value is less than one in a first temperature range and greater than one in a second temperature range higher than the first temperature range, that the reducing gas contains a hydrocarbon substance emitted from a plant or an animal.

A method of diagnosing a plant according to an embodiment of the present technology includes: heating a semiconductor sensor that includes an adsorption layer formed of a metal oxide in an area in which one or more plants to be tested are grown.

A resistance value of the semiconductor sensor in an air atmosphere in which a reducing gas is present is measured.

It is determined, where the measured resistance value is high in a first temperature range and low in a second temperature range higher than the first temperature range with reference to the resistance value of the semiconductor sensor in an air atmosphere in which the reducing gas is not present, that the reducing gas contains a hydrocarbon substance emitted from a plant or an animal, and a state of the plants in the area is diagnosed on the basis of detection information of a hydrocarbon substance emitted from the plants.

A gas detection method according to another embodiment of the present technology includes: heating a semiconductor sensor that includes an adsorption layer formed of a metal oxide in an area in which one or more plants to be tested are grown.

A resistance value of the semiconductor sensor in an air atmosphere in which a reducing gas is present is measured.

It is determined, where sensitivity that is a ratio of a resistance value the semiconductor sensor in the air atmosphere in which the reducing gas is not present to the measured resistance value is less than one in a first temperature range and greater than one in a second temperature range higher than the first temperature range, that the reducing gas contains a hydrocarbon substance emitted from a plant or an animal, and a state of the plants in the area is diagnosed on the basis of detection information of a hydrocarbon substance emitted from the plants.

A plant diagnosing apparatus according to an embodiment of the present technology includes: an acquisition unit; a determination unit; and a diagnosis unit.

In an area in which one or more plants to be tested are grown, the acquisition unit acquires a resistance value of a metal oxide semiconductor sensor in an air atmosphere in which a reducing gas is present.

The determination unit determines, where the acquired resistance value is high in a first temperature range and low in a second temperature range higher than the first temperature range with reference to the resistance value of the semiconductor sensor in an air atmosphere in which the reducing gas is not present, that the reducing gas contains a hydrocarbon substance emitted from a plant or an animal.

The diagnosis unit diagnoses a state of the plants in the area on the basis of detection information of a hydrocarbon substance emitted from the plants obtained by the determination unit.

A plant diagnosing apparatus according to another embodiment of the present technology includes: an acquisition unit; a determination unit; and a diagnosis unit.

In an area in which one or more plants to be tested are grown, the acquisition unit acquires a resistance value of a metal oxide semiconductor sensor in an air atmosphere in which a reducing gas is present.

The determination unit determines, where sensitivity that is a ratio of a resistance value of the semiconductor sensor in the air atmosphere in which the reducing gas is not present to the acquired resistance value is less than one in a first temperature range and greater than one in a second temperature range higher than the first temperature range, that the reducing gas contains a hydrocarbon substance emitted from a plant or an animal.

The diagnosis unit diagnoses a state of the plants in the area on the basis of detection information of a hydrocarbon substance emitted from the plants obtained by the determination unit.

MODE(S) FOR CARRYING OUT THE INVENTION

An embodiment according to the present technology will be described below with reference to the drawings.

[Semiconductor Sensor]

Figure 1:
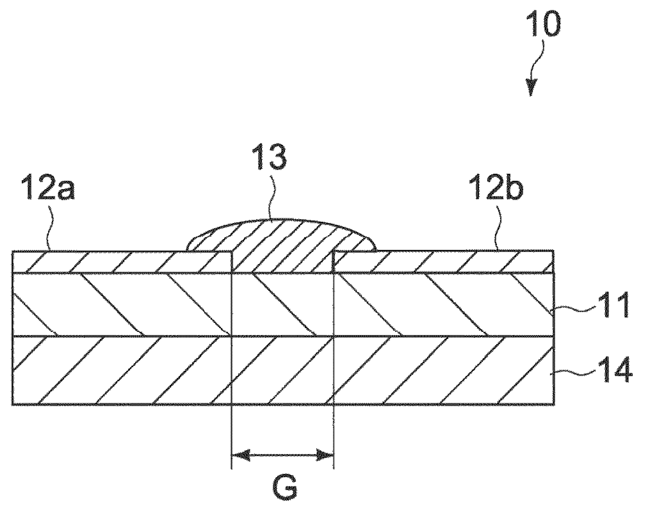
FIG. 1 is a schematic cross-sectional view showing a configuration of a main part of a semiconductor sensor to be used in an embodiment of the present technology.

FIG. 1 is a schematic cross-sectional view showing a configuration of a main part of a semiconductor sensor 10 to be used in an embodiment of the present technology.

The semiconductor sensor 10 includes a substrate 11, a pair of electrodes 12*a* and 12*b* formed on the front surface of the substrate 11, an adsorption layer 13 provided between the pair of electrodes 12*a* and 12*b*, and a heating layer 14 disposed on the back surface of the substrate 11.

The substrate 11 is, for example, an alumina substrate, a silicon substrate, or a quartz substrate.

The pair of electrodes 12*a* and 12*b* include, for example, a metal layer of Ti, Au, or s stacked film thereof, and are formed on the front surface of the substrate 11 with a gap G therebetween.

The adsorption layer 13 contains a metal oxide (MOx) including a sintered body containing a metal oxide material and a catalyst metal material. Examples of the metal oxide material include a tungsten oxide, an indium oxide, a tin oxide, and a zinc oxide. Examples of the catalyst metal material include iridium, an oxide thereof, palladium, an oxide thereof, rhenium, and an oxide thereof.

The heating layer 14 is for heating the adsorption layer 13 to a predetermined temperature and include, for example, a ceramic heater. The heating layer 14 is connected to a heater power source (not shown) and is configured to be heated to a temperature of, for example, 500° C. or less by a control device described below.

In general, when spraying a reducing gas while heating a MOx semiconductor sensor, the resistance value of the semiconductor sensor generally starts to change from a certain temperature. In this regard, a gas can be detected or quantified from the amount of change (sensitivity) in the resistance value. Further, when there is a large difference in profiles of the amount of change (sensitivity) in the temperature and resistance, the type of gas can be identified.

Figure 2:
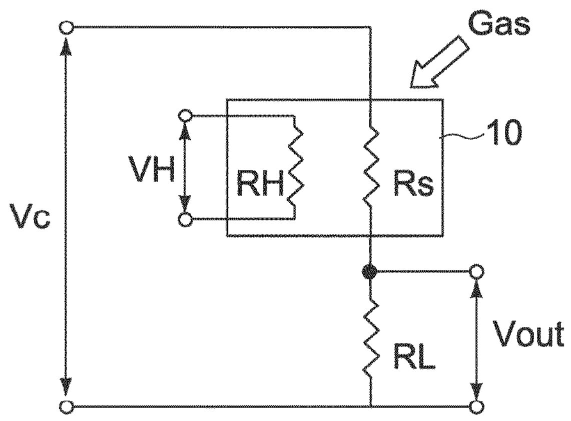
FIG. 2 is a drive circuit of the semiconductor sensor.

FIG. 2 is a drive circuit of the semiconductor sensor 10. In the figure, Rs is a sensor resistor, RL is a load resistor connected in series with the sensor resistor Rs, RH is a heater resistor for heating the semiconductor sensor 10, and the heating temperature of the heating layer 14 is adjusted by a heater voltage VH. Then, the sensor resistor Rs can be measured on the basis of a voltage Vout across the load resistor RL when a power supply voltage Vc is applied to both ends of the series resistors (Rs and RL) by the following formula.

$$Rs=((Vc-V\text{out})/V\text{out})\times RL$$

Figure 3:
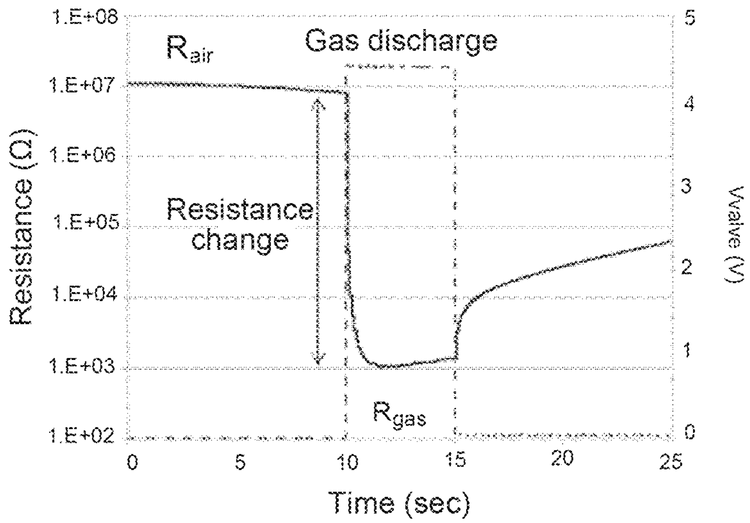
FIG. 3 is a diagram showing an example of a time change of a resistance value output from the semiconductor sensor.

FIG. 3 shows an example of a time change of a resistance value Rs output from the semiconductor sensor 10. In this example, the semiconductor sensor 10 was driven in an air atmosphere in which a reducing gas is not present, and a reducing gas was discharged into the air atmosphere for an arbitrary time (five seconds in this example).

Note that the air atmosphere in which a reducing gas is not present means a clean air atmosphere. The clean air atmosphere is typically a dry air atmosphere in which the temperature and humidity are controlled, for example. Here, the phrase "temperature and humidity are controlled" represents a controlled state in which a specific substance is removed by passing through a filter such as activated carbon, silica gel, and a molecular sieve by a pump. The specific substance is, for example, water vapor or VOC (volatile organic compound) in the environment.

Further, the dry air atmosphere here represents an air atmosphere in which the humidity is controlled at an arbitrary value.

As shown in FIG. 3, a resistance value Rgas of the semiconductor sensor 10 in the air atmosphere in which a reducing gas is present is lower than a resistance value Rair of the semiconductor sensor 10 in the clean air atmosphere. When the discharge of the reducing gas is stopped, the output of the semiconductor sensor 10 returns to the resistance value (Rair) in the clean air atmosphere.

The greater the decrease in Rgas with respect to Rair, the greater the sensitivity to the reducing gas. In the following description, the ratio of Rair to Rgas (Rair/Rgas) is defined as the sensor sensitivity.

Figure 4:
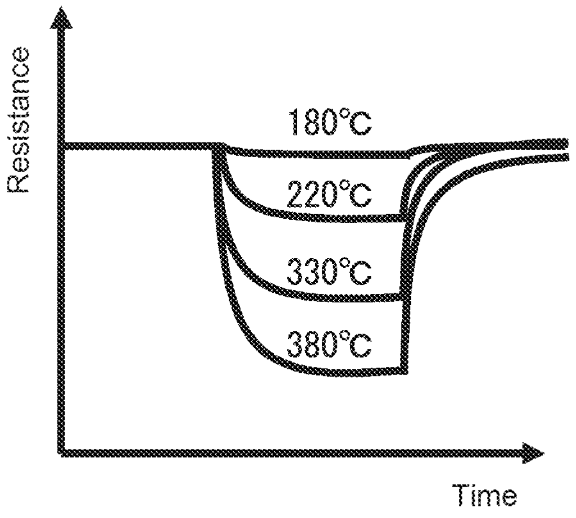
FIG. 4 is a schematic diagram showing a relationship between a heating temperature of the semiconductor sensor.
Figure 5:
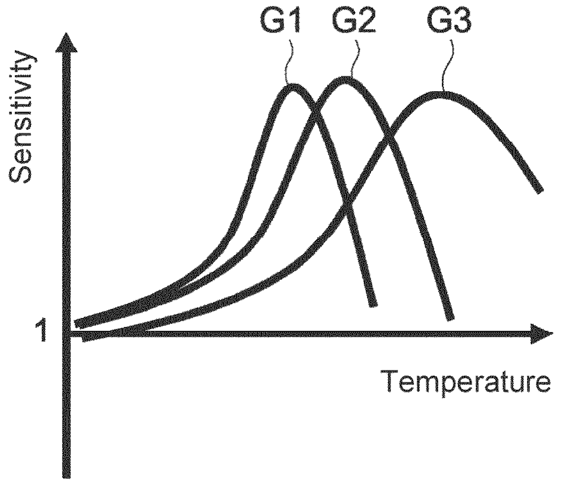
FIG. 5 is a schematic diagram showing a relationship between a heating temperature and sensitivity of the semiconductor sensor.

The resistance value and sensitivity of the semiconductor sensor 10 changes depending on the heating temperature of the heating layer 14. FIG. 4 is a schematic diagram showing a relationship between a heating temperature and a resistance value (hereinafter, referred to also as a resistance value profile). FIG. 5 is a schematic diagram showing a relationship between a heating temperature and sensitivity (hereinafter, referred to also as a sensitivity profile).

In the case of general reducing gases (e.g., hydrogen, acetone, ethanol, toluene, benzene, or cyclohexane), the semiconductor sensor 10 tends to have a larger amount of decrease in the resistance value and sensitivity of a value larger than one as the heating temperature rises as shown in FIG. 4 and FIG. 5. Further, as schematically shown in FIG. 5, it is possible to identify three different gas species G1, G2, and G3 on the basis of the difference in the sensitivity profile.

This type of change in the resistance value of the semiconductor sensor 10 due to the reducing gas is generally considered to be caused due to desorption/adsorption of oxygen accompanying oxidation-reduction of the metal oxide forming the adsorption layer 13.

For example, in the air atmosphere in which a reducing gas is not present, oxygen is adsorbed on the surface of the metal oxide particles to form a space charge layer in the vicinity of the surface of the particles. As a result, a potential barrier is formed at the grain boundary and hinders movement of electrons between the particles, thereby increasing the resistance value.

In this state, when a reducing gas is sprayed onto the semiconductor sensor 10, the oxygen adsorbed on the surface of the metal oxide particles is consumed, and thus, the space charge layer is thinned. As a result, the potential barrier is lowered, and thus, the resistance value is reduced.

Since the above-mentioned resistance value profile and sensitivity profile are unique to the gas species, it is theoretically possible to identify the gas species from the difference in these profiles. However, in the case where there is no sufficient difference in these profiles, it is difficult to identify the gas species with high accuracy.

Figure 6:
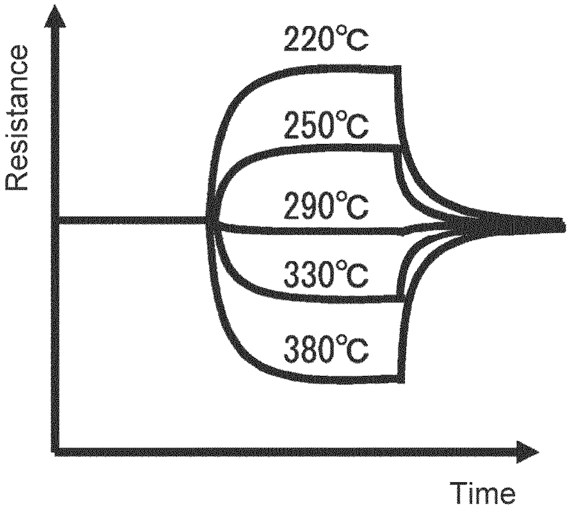
FIG. 6 is a schematic diagram showing a relationship between a heating temperature of the semiconductor sensor in the presence of a specific gas species.
Figure 7:
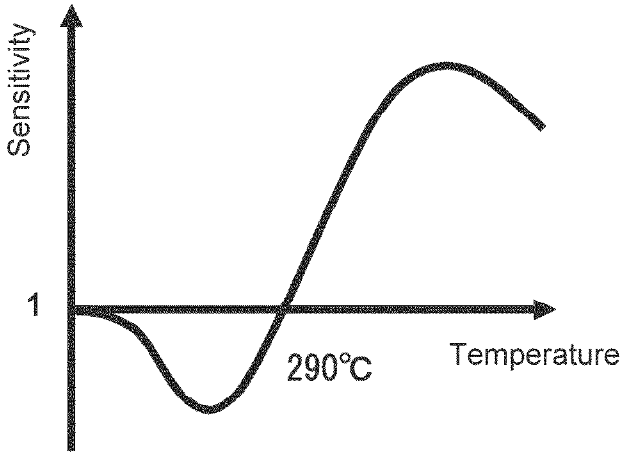
FIG. 7 is a schematic diagram showing a relationship between a heating temperature and sensitivity of the semiconductor sensor in the presence of a specific gas species.

Meanwhile, the present inventors have found that a specific type of reducing gas has a specific resistance value profile and sensitivity profile as schematically shown I FIG. 6 and FIG. 7.

That is, regarding the resistance value, the resistance value is higher in a certain temperature range (220° C. to 250° C. in the example of FIG. 6) and the resistance value is lower in a temperature range (290° ° C. to 380° C. in the same) higher than the temperature range. When this is converted into sensor sensitivity, the sensitivity is less than one in the temperature range described above and the sensitivity is greater than one in the higher temperature range (approximately 290° C. or more) as shown in FIG. 7.

Note that this is presumably because the gas species is adsorbed and attracts electrons from the semiconductor sensor in the low temperature range to increase the resistance and the gas species is decomposed in the high temperature range to decrease the resistance of the semiconductor sensor, although the details of the reason why such a specific profile appears are unknown.

Figure 8:
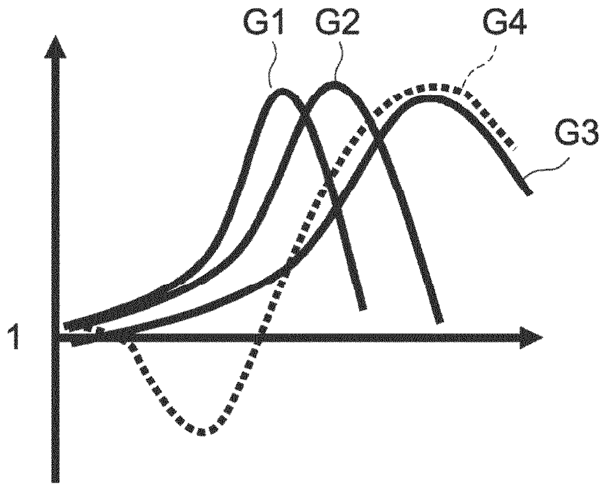
FIG. 8 is a schematic diagram describing a method of specifying a gas species using a difference in sensitivity.

As shown in FIG. 8, the gas species having a specific profile as described above is capable of easily identifying the specific gas species G4 by using the properties that the sensitivity shifts from decreasing to increasing.

Experimental Example

Figure 9:
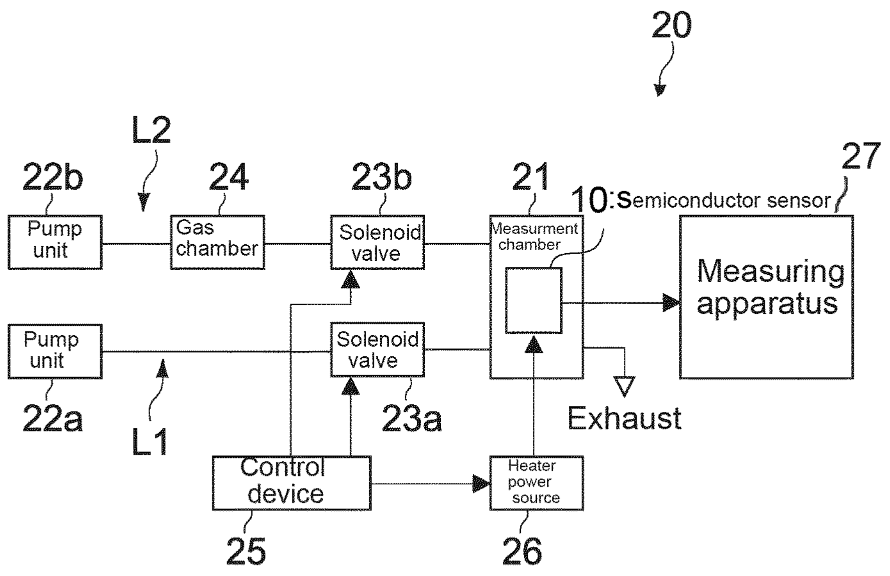
FIG. 9 is a schematic configuration diagram of a gas detection system.

The present inventors measured a change in the resistance value of various reducing gases by the semiconductor sensor 10 using the gas detection system shown in FIG. 9. FIG. 9 is a schematic configuration diagram of a gas detection system 20.

The semiconductor sensor 10 is placed in a measurement chamber 21. A dry air introduction line L1 and a reducing gas introduction line L2 are connected to the measurement chamber 21. In order to maintain the pressure inside the measurement chamber 21 constant, the gas introduced into the measurement chamber 21 is discharged from the measurement chamber 21.

The dry air introduction line L1 is configured to be capable of driving a pump unit 22*a* to introduce dry air (temperature of 25° C. and a relative humidity of 31%. The same applies hereinafter) into the measurement chamber 21 via a solenoid valve 23*a*.

The reducing gas introduction line L2 is configured to be capable of driving a pump unit 22*b* to introduce dry air into a gas chamber 24 filled with a reducing gas (saturated vapor) and introduce dry air containing a predetermined concentration of reducing gas into the measurement chamber 21 via a solenoid valve 23*b*.

The electrodes 12*a* and 12*b* of the semiconductor sensor 10 are each a rectangular Ti/Au film having a thickness of 200 nm and a size of 5 mm×4.5 mm, and have been disposed on the substrate 11 that has a thickness of 525 μm and is formed of alumina such that the long sides of the electrodes 12*a* and 12*b* face each other with the gap G of 5 μm sandwiched therebetween. The drive voltage Vc (see FIG. 2) to be input between the electrodes 12*a* and 12*b* was set to 5 V. The adsorption layer 13 is an n-type metal oxide semiconductor ($WO_3$—Pd) containing a tungsten oxide as a metal oxide material and palladium as a catalyst metal material, and has a thickness of several μm to 30 μm.

As the pump units 22*a* and 22*b*, commercially available pumps having a flow rate of 400 ml/min were used. The solenoid valves 23*a* and 23*b* are open/close valves capable of switching between two positions of fully open and fully closed.

A control device 25 controls the solenoid valves 23*a* and 23*b* and a heater power source 26 that heats the heating layer 14 (see FIG. 1) of the semiconductor sensor 10.

The control device 25 opens one of the solenoid valves 23*a* and 23*b* and closes the other to select one of the dry air introduction line L1 and the reducing gas introduction line L2.

The control device 25 controls the heater power source 26 to control the heating temperature of the semiconductor sensor 10. The heating temperature of the semiconductor sensor 10 is arbitrarily adjusted within the range of 40° ° C. to 500° C.

A measuring apparatus 27 acquires the resistance value Rs of the semiconductor sensor 10 at a plurality of temperatures within the heating temperature range on the basis of the output Vout (see FIG. 2) of the semiconductor sensor 10. The resistance value Rs corresponds to a resistance value in the air atmosphere in which a reducing gas is not present (Rair) when dry air is introduced from the dry air introduction line L1 into the measurement chamber 21 and a resistance value in the air atmosphere in which a reducing gas is present (Rgas) when a mixed gas of a reducing gas and dry air is introduced from the reducing gas introduction line L2 into the measurement chamber 21.

Using the gas detection system 20 configured as described above, the response properties of the semiconductor sensor 10 for a plurality of types of reducing gases were evaluated.

Figure 10:
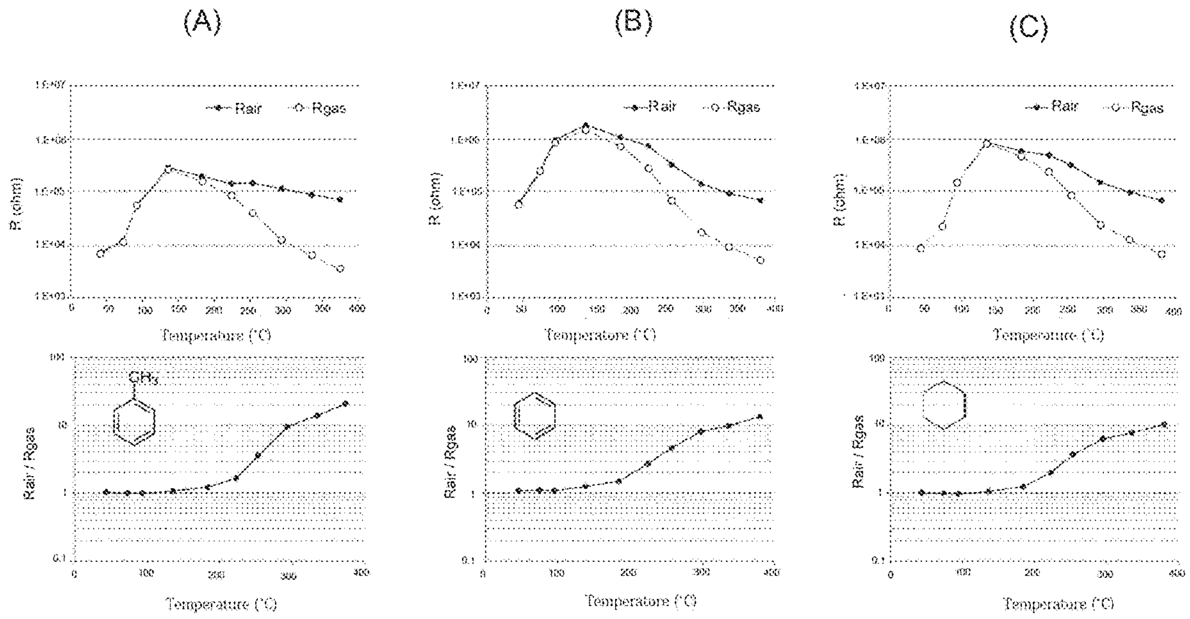
FIG. 10 is an experimental result showing a resistance value and sensitivity of the semiconductor sensor when (A) toluene, (B) benzene, and (C) cyclohexane are used as reducing gases.

FIG. 10 shows the resistance value profile (upper) and the sensitivity profile (lower) of the semiconductor sensor 10 when (A) toluene, (B) benzene, and (C) cyclohexane are used as reducing gases.

As shown in the figure, these gas species show a change in the resistance value at a heating temperature of 100° C. or more and show a tendency that the amount of decrease in the resistance value gradually increases as the heating temperature rises. Similarly, the sensor sensitivity tends to gradually increase as the heating temperature rises. The sensitivity profiles of these gas species match the aspects of the sensitivity profiles of the typical reducing gases shown in FIG. 5.

Figure 11:
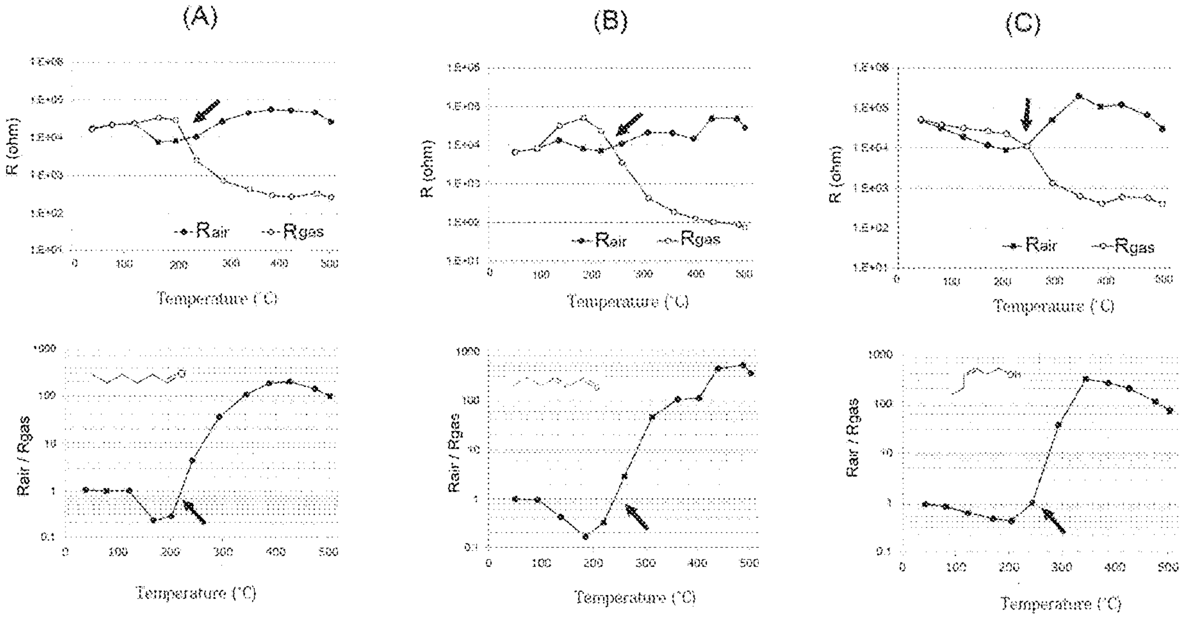
FIG. 11 is an experimental result showing a resistance value and sensitivity of the semiconductor sensor when (A) n-hexanal, (B) (E)-2-hexenal, (C) (Z)-3-hexenol are used as reducing gases.

Meanwhile, FIG. 11 shows the resistance value profile (upper) and the sensitivity profile (lower) of the semiconductor sensor 10 when (A) n-hexanal, (B) (E)-2-hexenal, and (C) (Z)-3-hexenol are used as reducing gases.

As shown in Parts (A), (B), and (C) of FIG. 11, for any of n-hexanal, (E)-2-hexenal, and (Z)-3-hexenol, in the first temperature range, the measured value (Rgas) of the semiconductor sensor 10 during spraying of the specific gas species tends to be higher than the measured value (Rair) before the spraying. Meanwhile, in the second temperature range higher than the first temperature range, the magnitude relationship between Rgas and Rair is reversed (higher temperature than the arrow in the figure), and Rgas is lower than Rair.

Similarly, as shown in Parts (A), (B), and (C) of FIG. 11, the sensor sensitivity is reduced to be less than one in the first temperature range, but increases to a value larger than one in the second temperature range (higher temperature than the arrow in the figure).

Note that the first temperature range described above is approximately 120° ° C. to approximately 220° ° C. in the case of n-hexanal, approximately 100° C. to approximately 250° C. in the case of (E)-2-hexenal, and approximately 60° C. to approximately 250° C. in the case of (Z)-3-hexenol.

Examples of the gas species having a specific resistance value profile and sensitivity profile as shown in Parts (A), (B), and (C) of FIG. 11 include a hydrocarbon substance emitted from a plant, such as (Z)-3-hexenyl acetate, α-pinene, and methyl salicylate as described below, in addition to the above.

The change in the resistance value of various reducing gases by the semiconductor sensor 10 of (Z)-3-hexenylacetate and α-pinene as describe above is shown below.

Although the experimental conditions are substantially the same as those of the above-mentioned experimental example, the difference is that the metal oxide material of the adsorption layer 13 is a zinc oxide.

Figure 12:
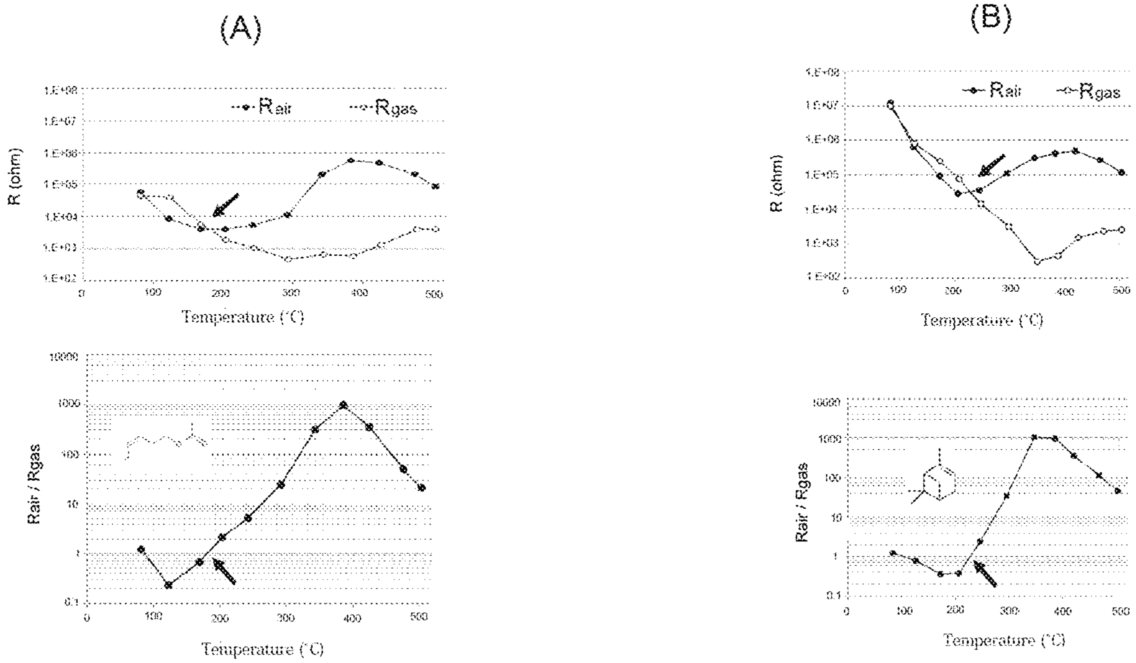
FIG. 12 is an experimental result showing a resistance value and sensitivity of the semiconductor sensor when (A) (Z)-3-hexenyl acetate and (B) α-pinene are used as reducing gases.

Then, FIG. 12 shows the resistance value profile (upper) and the sensitivity profile (lower) of the semiconductor sensor 10 when (A) (Z)-3-hexenylacetate and (B) α-pinene are used as reducing gases.

As shown in Parts (A) and (B) of FIG. 12, for any of (Z)-3-hexenylacetate and α-pinene, in the first temperature range, the measured value (Rgas) of the semiconductor sensor 10 during spraying of the specific gas species tends to be higher than the measured value (Rair) before the spraying. Meanwhile, in the second temperature range higher than the first temperature range, the magnitude relationship between Rgas and Rair is reversed (higher temperature than the arrow in the figure), and Rgas is lower than Rair.

Similarly, the sensor sensitivity is reduced to be less than one in the first temperature range, but increases to a value larger than one in the second temperature range (higher temperature than the arrow in the figure) as shown in Parts (A) and (B) of FIG. 12.

Note that the first temperature range described above is approximately 80° ° C. to approximately 180° C. in the case of (Z)-3-hexenylacetate and approximately 80° C. to approximately 230° C. in the case of α-pinene.

The change in the resistance value of the educing gas by the semiconductor sensor 10 of methyl salicylate as describe above is shown below.

Although the experimental conditions are substantially the same as those of the above-mentioned experimental example, the difference is that the adsorption layer 13 contains a tungsten oxide as a metal oxide material and rhenium as a catalyst metal material.

Figure 20:
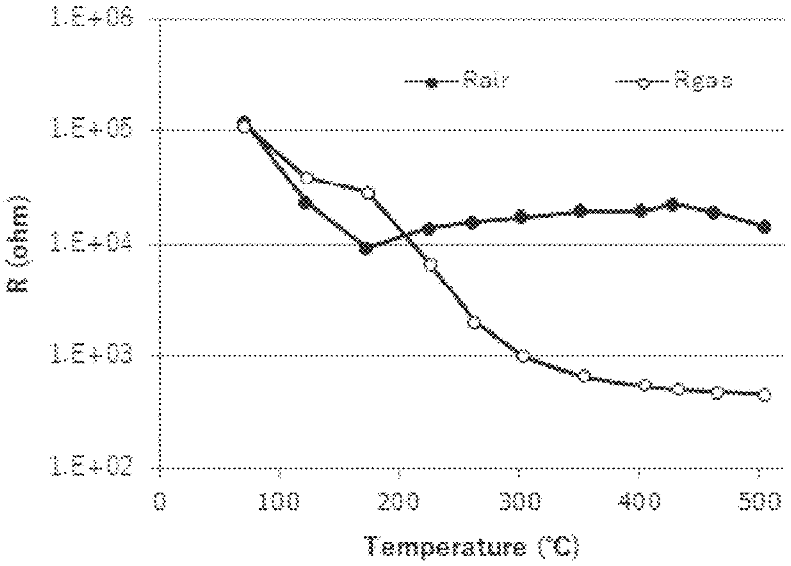
FIG. 20 is an experimental result showing a resistance value and sensitivity of the semiconductor sensor when methyl salicylate is used as a reducing gas.
Figure 20:
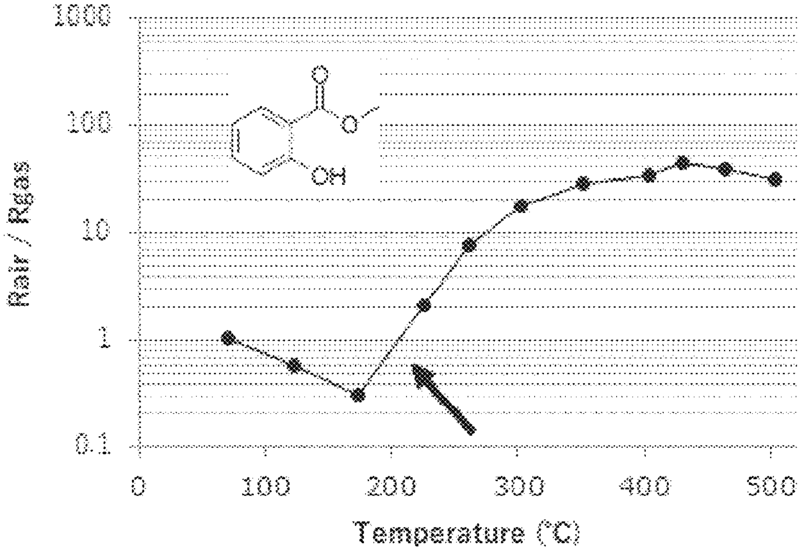

Then, FIG. 20 shows the resistance value profile (upper) and the sensitivity profile (lower) of the semiconductor sensor 10 when methyl salicylate is used as a reducing gas.

As shown in FIG. 20, also for methyl salicylate, in the first temperature range, the measured value (Rgas) of the semiconductor sensor 10 during spraying of the specific gas species tends to be higher than the measured value (Rair) before the spraying. Meanwhile, in the second temperature range higher than the first temperature range, the magnitude relationship between Rgas and Rair is reversed (higher temperature than the arrow in the figure), and Rgas is lower than Rair.

Similarly, the sensor sensitivity is reduced to be less than one in the first temperature range, but increases to a value larger than one in the second temperature range (higher temperature than the arrow in the figure) as shown in FIG. 20.

Note that the first temperature range described above is approximately 80° C. to approximately 220° C.

[Gas Detection Method]

Application example of the semiconductor sensor 10 include a detection apparatus having a function of detecting plant damage by pests described below.

In the case where plants are cultivated throughout agriculture including plant factories, the above-mentioned gas detection method can also be applied to detect plant damages by pests.

It is known that plants release volatile molecules called green leaf volatiles (GLVs) when they are damaged by pests. The green leaf volatiles are the main component of green leaf scent and grassy smell, and approximately nine types, (Z)-3-hexenal, (Z)-3-hexenol, (Z)-3-hexenyl acetate, (E)-2-hexenal, (E)-2-hexenol, (E)-2-hexenyl acetate, n-hexanal, n-hexanol, and n-hexanyl acetate, are currently known. In addition, it is known that plants release volatile chemical substances that act to attract predators of herbivores (such as parasitic wasps), which are specifically produced when plants are damaged by pests or the like, such as herbivore-induced plant volatiles (HIPVs). The classification thereof includes many terpenes and terpenoids, it has the characteristic of releasing a unique blend of odors in accordance with the type of pest, and α-pinene, d-limonene, (Z)-β-ocimene, jasmonic acid, and the like are known.

In addition to the above, there is methyl salicylate as a volatile molecule that is likely to be released when plants are diseased (pathogen infection). Methyl salicylate is also known as a substance involved in plant-to-plant communication.

In the past, a method of preparing a molecular template polymer on which a specific volatile substance is adsorbed, causing a target volatile substance to be adsorbed on the molecular template polymer in advance, and detecting only the volatile substance by a MOx sensor has been known as a method of detecting damage caused by pests, but has the following problems.

- It is necessary to prepare a molecular template polymer for each volatile substance to be measured, and volatile substances having different molecular structures cannot be adsorbed by the same molecular template polymer.
- Since the molecular template polymer has a macromolecule, it has poor long-term stability under high temperature and high humidity conditions.

The detection method described above causes a volatile substance to be selectively adsorbed on a molecular template polymer and detects the volatile substance by a MOx sensor. However, in the present technology, a hydrocarbon substance emitted from plants, which is called "green leaf volatiles" or "herbivore-induced plant volatiles", is detected on the basis of the difference in temperature/sensitivity profile of the MOx sensor, and the hydrocarbon substance can be detected only by the MOx sensor without using a molecular template polymer.

Here, the hydrocarbon substance may be a C6 linear aliphatic compound, a terpene, or terpenoids, and the molecular weight thereof is typically 50 or more and 250 or less, and in the range of approximately 90 or more and 160 or less, specifically 98 or more and 152 or less in the case of the substance adopted in the experimental example described above.

In accordance with the above-mentioned gas detection method, by detecting the hydrocarbon substance described above, it is possible to detect plant damage by pests at an early stage and take countermeasures at an early stage.

In order to identify a gas species, the resistance value profile of the semiconductor sensor 10 may be referred to or the sensitivity profile may be referred to.

In the case of referring to a resistance value profile, the semiconductor sensor 10 including an adsorption layer formed of a metal oxide is heated, the resistance value (Rgas) of the semiconductor sensor 10 in the air atmosphere in which a reducing gas is present is measured, and it is determined, in the case where the resistance value (Rgas) is high in the first temperature range and low in the second temperature range higher than the first temperature range with reference to the resistance value (Rair) of the semiconductor sensor 10 in the air atmosphere in which a reducing gas is not present, that the reducing gas contains a hydrocarbon substance emitted from plants.

Meanwhile, in the case of referring to the sensitivity profile, the semiconductor sensor 10 including an adsorption layer formed of a metal oxide is heated, the resistance value (Rgas) of the semiconductor sensor 10 in the air atmosphere in which a reducing gas is present is measured, and it is determined, in the case where the sensitivity (Rair/Rgas) that is the ratio of the resistance value of the semiconductor sensor 10 in the air atmosphere in which a reducing gas is not present with respect to the measured resistance value (Rgas) is less than one in the first temperature range and is larger than one in the second temperature range higher than the first temperature range, that the reducing gas contains a hydrocarbon substance emitted from plants.

(Information Processing Apparatus)

In the above-mentioned gas detection system, the measuring apparatus 27 can be configured as a detection apparatus of a reducing gas containing a hydrocarbon substance emitted from plants.

Figure 13:
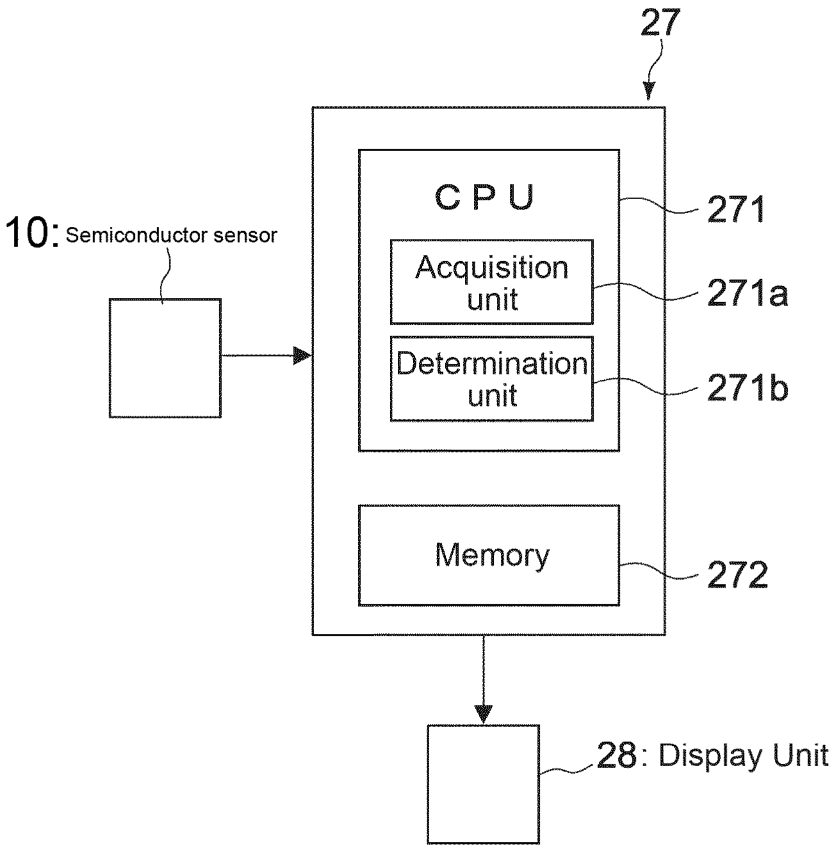
FIG. 13 is a schematic configuration diagram of gas detection apparatus.

FIG. 13 is a schematic configuration diagram of the measuring apparatus 27. The measuring apparatus 27 includes a computer (information processing apparatus) including a CPU 271 and a memory 272.

The CPU 271 includes an acquisition unit 271*a* and a determination unit 271*b*. The acquisition unit 271*a* acquires the resistance value Rgas of the semiconductor sensor 10 in the air atmosphere in which a reducing gas is present.

The acquisition unit 271*a* may include a calculation unit that converts the output (Vout) of the semiconductor sensor 10 into the resistance value Rgas.

The determination unit 271*a* is configured to determine, on the basis of the resistance value Rgas of the semiconductor sensor 10 acquired by the acquisition unit 271*a*, whether or not the resistance value profile or sensitivity profile thereof is a predetermined profile.

The memory 272 is an information storage device such as a semiconductor memory and a hard disk. The memory 272 stores a program for causing the acquisition unit 271*a* and the determination unit 271*b* to operate as functional blocks of the CPU 271. Further, the memory 272 stores data relating to the resistance value profile and the sensitivity profile of the semiconductor sensor 10 in the air atmosphere in which a reducing gas is not present.

The output of the measuring apparatus 27 may be displayed on a display unit 28. The display unit 28 displays, for example, the resistance value profile and the sensitivity profile of the semiconductor sensor 10 as shown in FIG. 10 and FIG. 11.

(Processing Procedure 1)

Figure 14:
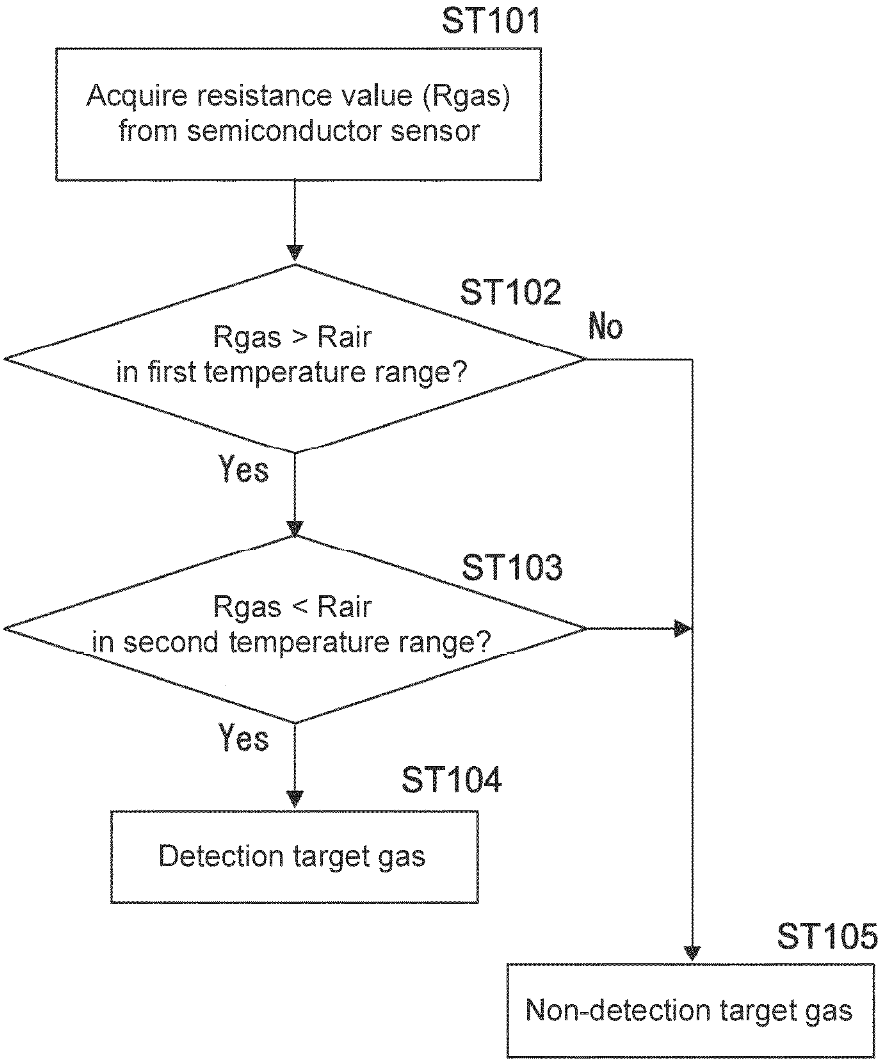
FIG. 14 is a flowchart showing an example of the processing procedure of the gas detection apparatus.

FIG. 14 is a flowchart showing an example of the processing procedure executed in the CPU 271.

First, the acquisition unit 271*a* acquires the resistance value (Rgas) of the semiconductor sensor 10 in the air atmosphere containing a reducing gas (Step 101).

Subsequently, the determination unit 271*b* determines whether or not the measured resistance value (Rgas) is high in the first temperature range with reference to the resistance value (Rair) of the semiconductor sensor in the air atmosphere in which a reducing gas is not present (Step 102).

In the case where Rgas>Rair ("Yes" in Step 102), the determination unit 271*b* further determines whether or not the measured resistance value (Rgas) is low in the second temperature range higher than the first temperature range with reference to the resistance value (Rair) of the semiconductor sensor in the air atmosphere in which a reducing gas is not present (Step 103).

Then, the determination unit 271*b* determines, in the case where both Steps 102 and 103 are "Yes", that the reducing gas is a detection target gas (gas containing a hydrocarbon substance emitted from plants) (Step 104) and determines, in the case where at least one of Steps 102 and 103 is "No", that the reducing gas is a non-detection target gas (gas that does not contain a hydrocarbon substance emitted from plants) (Step 105).

(Processing Procedure 2)

Figure 15:
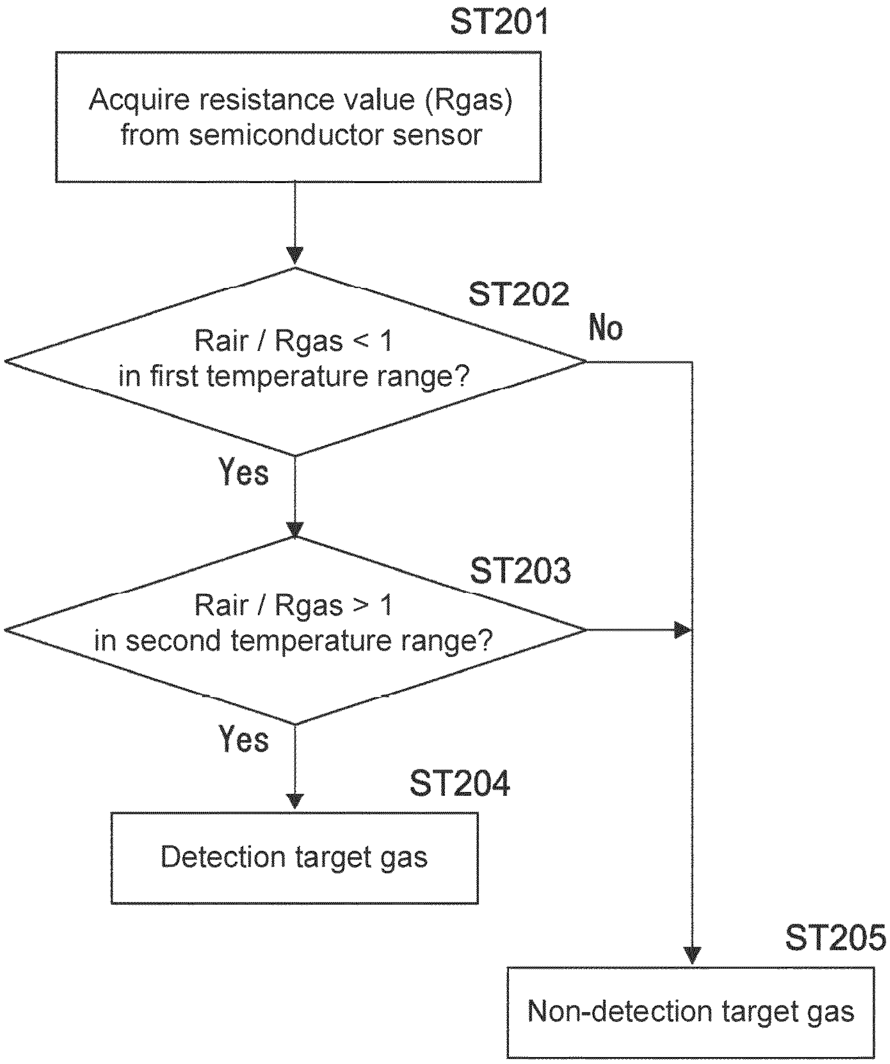
FIG. 15 is a flowchart showing another example of the processing procedure of the gas detection apparatus.

FIG. 15 is a flowchart showing another example of the processing procedure executed in the CPU 271.

First, the acquisition unit 271*a* acquires the resistance value (Rgas) of the semiconductor sensor 10 in the air atmosphere containing a reducing gas (Step 201).

Subsequently, the determination unit 271*b* determines whether or not the sensitivity (Rair/Rgas) that is the ratio of the resistance value (Rair) of the semiconductor sensor in the air atmosphere in which a reducing gas is not present with respect to the measured resistance value (Rgas) is less than one in the first temperature range (Step 202).

In the case where Rair/Rgas<1 ("Yes" in Step 202), the determination unit 271*b* further determines whether or not the sensitivity (Rair/Rgas) is larger than one in the second temperature range higher than the first temperature range (Step 203).

Then, the determination unit 271*b* determines, in the case where both Steps 202 and 203 are "Yes", that the reducing gas is a detection target gas (gas containing a hydrocarbon substance emitted from plants) (Step 204), and determines, in the case where at least one of Steps 202 and 203 is "No", that the reducing gas is a non-detection target gas (gas that does not contain a hydrocarbon substance emitted from plants) (Step 205).

[Method of Diagnosing Plant]

Other application examples of the semiconductor sensor 10 include a detection apparatus having a function of diagnosing plants as described below.

In an area in which one or more plants to be tested are grown, the above-mentioned gas detection method is applied to detect the presence or absence of a hydrocarbon substance emitted from plants, such as the above-mentioned green leaf volatiles and herbivore-induced plant volatiles, and diagnose the presence or absence of plant damage by pests.

In order to identify a gas species, the resistance value profile of the semiconductor sensor 10 may be referred to or the sensitivity profile may be referred to.

In the case of referring to a resistance value profile, the semiconductor sensor 10 including an adsorption layer formed of a metal oxide is heated, the resistance value (Rgas) of the semiconductor sensor 10 in the air atmosphere in which a reducing gas is present is measured, it is determined, in the case where the measured resistance value (Rgas) is high in the first temperature range and low in the second temperature range higher than the first temperature range with reference to the resistance value (Rair) of the semiconductor sensor 10 in the air atmosphere in which a reducing gas is not present, the reducing gas contains a hydrocarbon substance emitted from plants, and the state of plants in the area in which one or more plants to be tested are grown is diagnosed on the basis of detection information of the hydrocarbon substance emitted from plants.

Meanwhile, in the case of referring to the sensitivity profile, the semiconductor sensor 10 including an adsorption layer formed of a metal oxide is heated, the resistance value (Rgas) of the semiconductor sensor 10 in the air atmosphere in which a reducing gas is present is measured, it is determined, in the case where the sensitivity (Rair/Rgas) that is the ratio of the resistance value of the semiconductor sensor 10 in the air atmosphere in which a reducing gas is not present with respect to the measured resistance value is less than one in the first temperature range and is larger than one in the second temperature range higher than the first temperature range, that the reducing gas contains a hydrocarbon substance emitted from plants, and the state of plants in the area described above is diagnosed on the basis of detection information of the hydrocarbon substance emitted from plants.

(Plant Diagnosing Apparatus)

In the above-mentioned gas detection system, a plant diagnosing apparatus 27A can be configured as a detection apparatus of a reducing gas containing a hydrocarbon substance emitted from plants, such as the above-mentioned green leaf volatiles and herbivore-induced plant volatiles.

Figure 16:
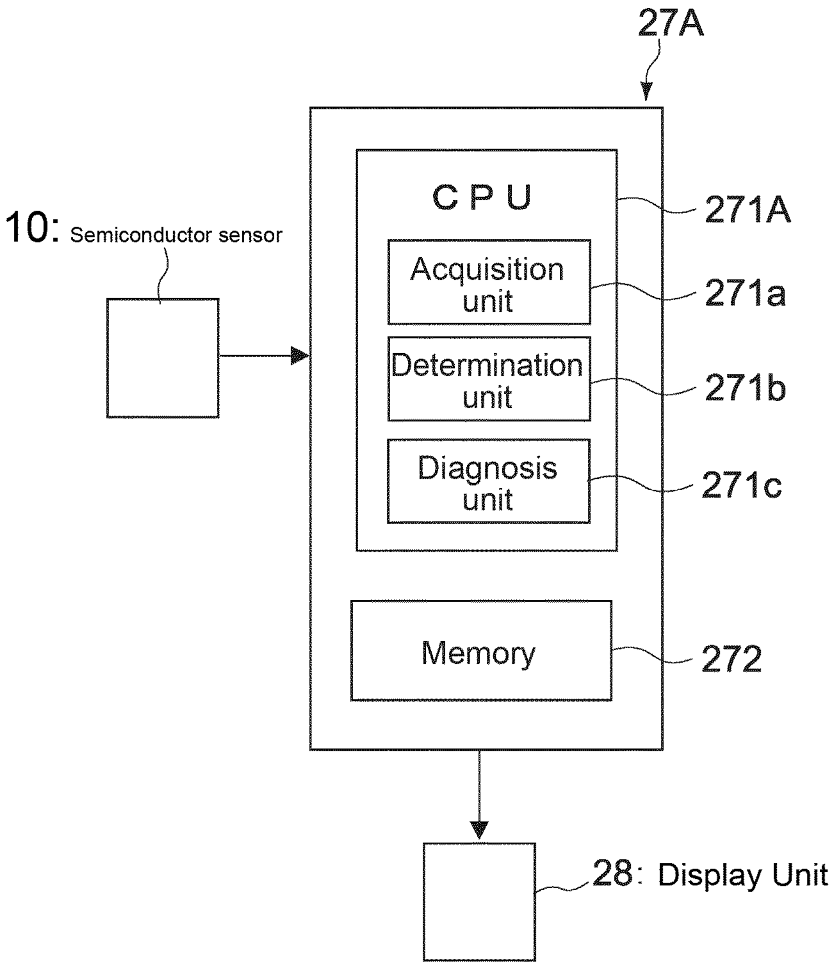
FIG. 16 is a schematic configuration diagram of a plant diagnosing apparatus.

FIG. 16 is a schematic configuration diagram of the plant diagnosing apparatus 27A. The plant diagnosing apparatus 27A includes a computer (information processing apparatus) including the CPU 271 and the memory 272.

The CPU 271A includes the acquisition unit 271*a*, the determination unit 271*b*, and a diagnosis unit 271*c*. The acquisition unit 271*a* acquires the resistance value Rgas of the semiconductor sensor 10 in the air atmosphere in which a reducing gas is present.

The acquisition unit 271*a* may include a calculation unit that converts the output (Vout) of the semiconductor sensor 10 into the resistance value Rgas.

The determination unit 271*b* is configured to determine, on the basis of the resistance value Rgas of the semiconductor sensor 10 acquired by the acquisition unit 271*a*, whether or not the resistance value profile or the sensitivity profile is a predetermined profile.

The diagnosis unit 271*c* diagnoses the state of plants in the area in which one or more plants to be tested are grown by the determination result (detection information of a hydrocarbon substance emitted from plants) of the determination unit 271*b*.

The memory 272 is an information storage device such as a semiconductor memory and a hard disk. The memory 272 stores a program for causing the acquisition unit 271*a*, the determination unit 271*b*, and the diagnosis unit 271*c* to operate as functional blocks of the CPU 271. Further, the memory 272 stores the resistance value profile and the sensitivity profile of the semiconductor sensor 10 in the air atmosphere in which a reducing gas is not present.

The output of the plant diagnosing apparatus 27A may be displayed on the display unit 28. The display unit 28 displays, for example, the presence or absence of plant damage by pests by the diagnosis unit 271*c*.

(Diagnosis Procedure 1)

Figure 17:
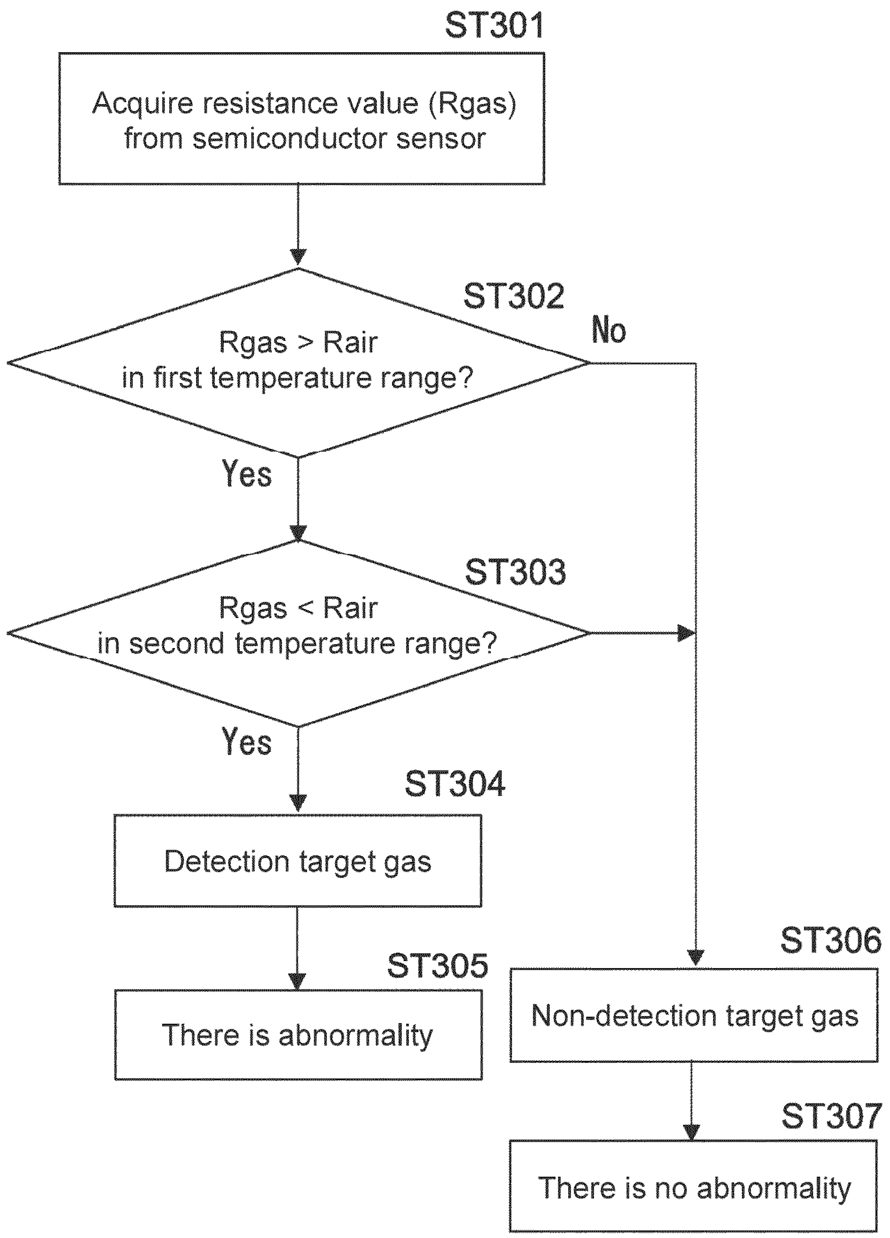
FIG. 17 is a flowchart showing an example of the processing procedure of the plant diagnosing apparatus.

FIG. 17 is a flowchart showing an example of the diagnosis procedure executed in the CPU 271A.

Step 301 to Step 304 and Step 306 shown in FIG. 17 are respectively similar to Step 101 to Step 104 and Step 105 of the above-mentioned processing procedure of the gas detection apparatus shown in FIG. 14, and the diagnosis unit 271*c* diagnoses, in the case where it is determined that a hydrocarbon substance emitted from plants is contained (Step 304), that there is an abnormality (Step 305). Further, in the case where it is determined that a hydrocarbon substance emitted from plants is not contained (Step 306), the diagnosis unit 271*c* diagnoses that there is no abnormality (Step 307).

(Diagnosis Procedure 2)

Figure 18:
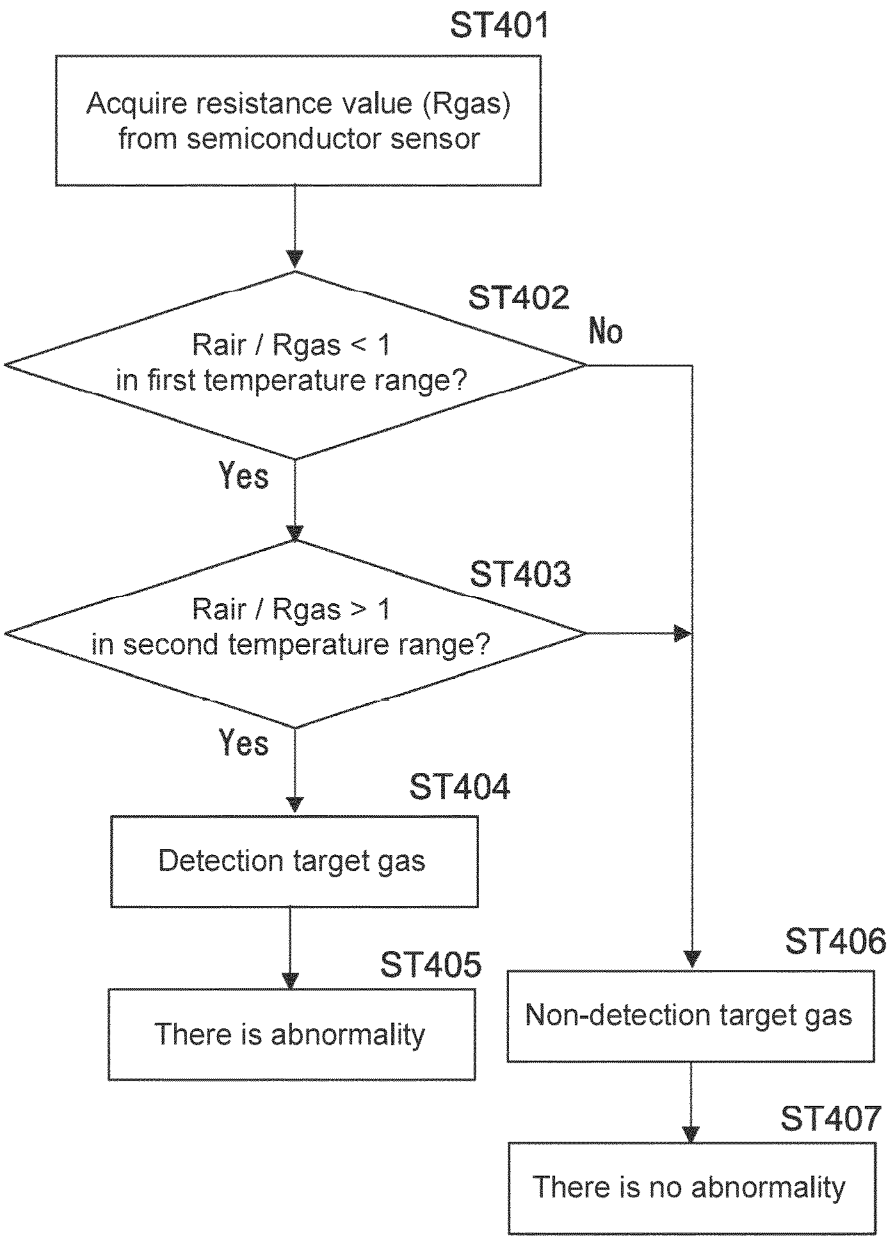
FIG. 18 is a flowchart showing another example of the processing procedure of the plant diagnosing apparatus.

FIG. 18 is a flowchart showing another example of the diagnosis procedure executed in the CPU 271A.

Step 401 to Step 404 and Step 406 shown in FIG. 18 are similar to Step 201 to Step 204 and Step 205 of the above-mentioned processing procedure of the gas detection apparatus shown in FIG. 14, and the diagnosis unit 271*c* diagnoses, in the case where it is determined that a hydrocarbon substance emitted from plants is contained (Step 404), that there is abnormality (Step 405). Further, in the case where it is determined that a hydrocarbon substance emitted from plants is not contained (Step 406), the diagnosis unit 271*c* diagnoses that there is no abnormality (Step 407).

The first and second temperature ranges described above may be set in advance, but after acquiring all measured values at each temperature, whether or not there is an area corresponding to the first and second temperature ranges may be determined.

Further, the resistance value of the semiconductor sensor 10 at each heating temperature may be a resistance value measured at a predetermined sampling period while heating the semiconductor sensor 10 at a predetermined heating rate.

Alternatively, a plurality of semiconductor sensors 10 may be prepared and measured values when the plurality of semiconductor sensors is heated to different heating temperatures may be used.

Modified Example

Although a hydrocarbon substance emitted from plants has been described above as an example in the example of the present technology, the present technology is not limited thereto. For example, a hydrocarbon substance emitted from animals may be detected by a MOx sensor according to the present technology. The hydrocarbon substance emitted from animals is, for example, nonanal, and can be detected by the MOx sensor to diagnose lung cancer.

Application Example

Although a hydrocarbon substance emitted from plants is detected only by the MOx sensor in the example of the present technology, the present technology is not limited thereto.

Figure 19:
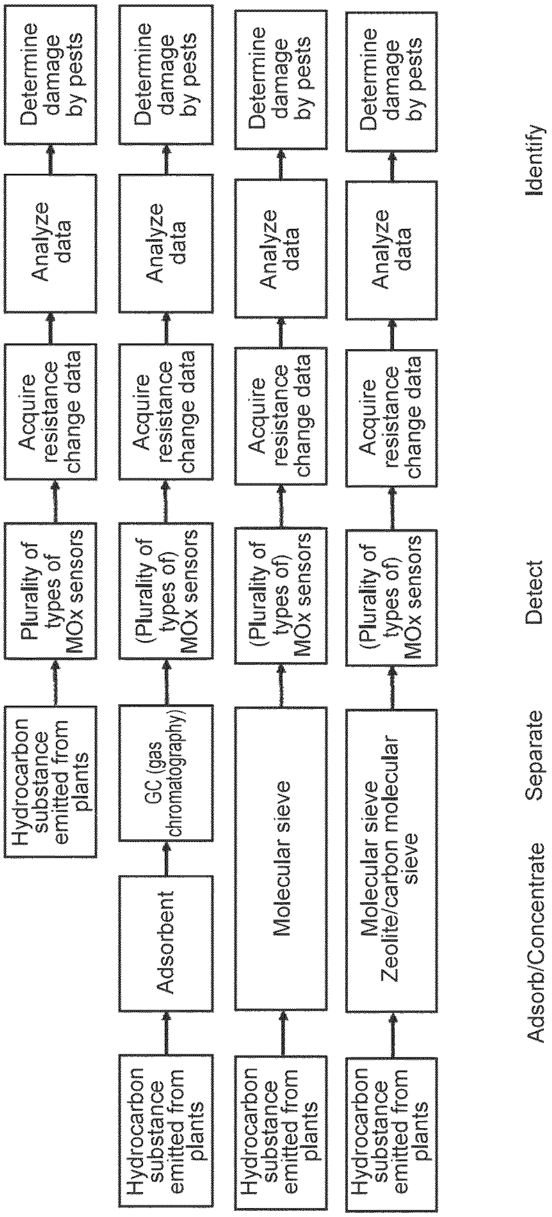
FIG. 19 is a process of determining the presence or absence of plant damage by pests.

For example, FIG. 19 shows a process of determining the presence or absence of plant damage by pests. As shown in FIG. 19, a hydrocarbon substance emitted from plants may be adsorbed, concentrated, and separated by gas chromatography, molecular sieve (zeolite/carbon molecular sieve), or the above-mentioned molecular template polymer and then detected by the MOx sensor according to the present technology. As a result, it is possible to improve the detection accuracy of the MOx sensor according to the present technology.

It should be noted that the present technology may also take the following configurations.

(1) A gas detection method, including:
- heating a semiconductor sensor that includes an adsorption layer formed of a metal oxide;
- measuring a resistance value of the semiconductor sensor in an air atmosphere in which a reducing gas is present;
- determining, where the measured resistance value is high in a first temperature range and low in a second temperature range higher than the first temperature range with reference to the resistance value of the semiconductor sensor in an air atmosphere in which the reducing gas is not present, that the reducing gas contains a hydrocarbon substance emitted from a plant or an animal.

(2) The gas detection method according to (1) above, in which
- the air atmosphere in which the reducing gas is not present is dry air.

(3) The gas detection method according to (1) or (2) above, in which the semiconductor sensor includes a plurality of semiconductor sensors, the step of heating the semiconductor sensor includes heating each of the plurality of semiconductor sensors to different heating temperatures, and the step of measuring a resistance value of the semiconductor sensor includes measuring a resistance value of each of the plurality of semiconductor sensors.

(4) The gas detection method according to any one of (1) to (3) above, in which the hydrocarbon substance is a substance containing a C6 linear aliphatic compound.

(5) The gas detection method according to any one of (1) to (4) above, in which the hydrocarbon substance has a molecular weight of 90 or more and 160 or less.

(6) The gas detection method according to any one of (1) to (5) above, in which the metal oxide is a sintered body containing a metal oxide material and a catalyst metal material.

(7) The gas detection method according to (6) above, in which the metal oxide material includes a tungsten oxide, an indium oxide, a tin oxide, or a zinc oxide, and the catalyst metal material includes iridium, an oxide thereof, palladium, an oxide thereof, rhenium, or an oxide thereof.

(8) A gas detection method, including:

heating a semiconductor sensor that includes an adsorption layer formed of a metal oxide;

measuring a resistance value of the semiconductor sensor in an air atmosphere in which a reducing gas is present;

determining, where sensitivity that is a ratio of a resistance value the semiconductor sensor in the air atmosphere in which the reducing gas is not present to the measured resistance value is less than one in a first temperature range and greater than one in a second temperature range higher than the first temperature range, that the reducing gas contains a hydrocarbon substance emitted from a plant or an animal.

(9) An information processing apparatus, including:

an acquisition unit that acquires a resistance value of a metal oxide semiconductor sensor in an air atmosphere in which a reducing gas is present; and a determination unit that determines, where the acquired resistance value is high in a first temperature range and low in a second temperature range higher than the first temperature range with reference to the resistance value of the semiconductor sensor in an air atmosphere in which the reducing gas is not present, that the reducing gas contains a hydrocarbon substance emitted from a plant or an animal.

(10) An information processing apparatus, including:

an acquisition unit that acquires a resistance value of a metal oxide semiconductor sensor in an air atmosphere in which a reducing gas is present; and a determination unit that determines, where sensitivity that is a ratio of a resistance value of the semiconductor sensor in the air atmosphere in which the reducing gas is not present to the acquired resistance value is less than one in a first temperature range and greater than one in a second temperature range higher than the first temperature range, that the reducing gas contains a hydrocarbon substance emitted from a plant or an animal.

(11) A method of diagnosing a plant, including, in an area in which one or more plants to be tested are grown:

heating a semiconductor sensor that includes an adsorption layer formed of a metal oxide;

measuring a resistance value of the semiconductor sensor in an air atmosphere in which a reducing gas is present;

determining, where sensitivity that is a ratio of a resistance value the semiconductor sensor in the air atmosphere in which the reducing gas is not present to the measured resistance value is less than one in a first temperature range and greater than one in a second temperature range higher than the first temperature range, that the reducing gas contains a hydrocarbon substance emitted from a plant or an animal; and diagnosing a state of the plants in the area on the basis of detection information of a hydrocarbon substance emitted from the plants.

(12) A method of diagnosing a plant, including, in an area in which one or more plants to be tested are grown:

heating a semiconductor sensor that includes an adsorption layer formed of a metal oxide;

measuring a resistance value of the semiconductor sensor in an air atmosphere in which a reducing gas is present;

determining, where sensitivity that is a ratio of a resistance value the semiconductor sensor in the air atmosphere in which the reducing gas is not present to the measured resistance value is less than one in a first temperature range and greater than one in a second temperature range higher than the first temperature range, that the reducing gas contains a hydrocarbon substance emitted from plants; and diagnosing a state of the plants in the area on the basis of detection information of a hydrocarbon substance emitted from the plants.

(13) A plant diagnosing apparatus, including, in an area in which one or more plants to be tested are grown:

an acquisition unit that acquires a resistance value of a metal oxide semiconductor sensor in an air atmosphere in which a reducing gas is present;

a determination unit that determines, where sensitivity that is a ratio of a resistance value of the semiconductor sensor in the air atmosphere in which the reducing gas is not present to the acquired resistance value is less than one in a first temperature range and greater than one in a second temperature range higher than the first temperature range, the reducing gas contains a hydrocarbon substance emitted from plants; and a diagnosis unit that diagnoses a state of the plants in the area on the basis of detection information of a hydrocarbon substance emitted from the plants obtained by the determination unit. (14) A plant diagnosing apparatus, including, in an area in which one or more plants to be tested are grown;

an acquisition unit that acquires a resistance value of a metal oxide semiconductor sensor in an air atmosphere in which a reducing gas is present;

a determination unit that determines, where the acquired resistance value is high in a first temperature range and low in a second temperature range higher than the first temperature range with reference to the resistance value of the semiconductor sensor in an air atmosphere in which the reducing gas is not present, that the reducing gas contains a hydrocarbon substance emitted from a plant or an animal; and a diagnosis unit that diagnoses a state of the plants in the area on the basis of detection information of a hydrocarbon substance emitted from the plants obtained by the determination unit.

REFERENCE SIGNS LIST

10 semiconductor sensor
11 substrate
12*a*, 12*b* electrode
13 adsorption layer
14 heating layer
20 gas detection system
27 measuring apparatus
271*a* acquisition unit
271*b* determination unit

The invention claimed is:

1. A gas detection method, comprising:

heating at least one semiconductor sensor that includes an adsorption layer formed of a metal oxide including a metal oxide material and a catalyst metal material;

measuring a resistance value of the semiconductor sensor in an air atmosphere in which a reducing gas is present;

determining, where the measured resistance value in a first temperature range from 80° C. to 220° C. is higher than in a second temperature range from 290° C. or greater with reference to a resistance value of the semiconductor sensor in an air atmosphere in which the reducing gas is not present, that the reducing gas contains a hydrocarbon substance emitted from a plant or an animal, wherein the metal oxide material includes a tungsten oxide, and wherein the catalyst metal material includes rhenium.

2. The gas detection method according to claim 1, wherein the air atmosphere in which the reducing gas is not present is dry air.

3. The gas detection method according to claim 1, wherein the at least one semiconductor sensor is a plurality of semiconductor sensors, heating each of the plurality of semiconductor sensors to different heating temperatures, and measuring a resistance value of each of the plurality of semiconductor sensors.

4. The gas detection method according to claim 1, wherein the hydrocarbon substance has a molecular weight of 90 or more and 160 or less.

5. The gas detection method according to claim 1, wherein the metal oxide is a sintered body including the metal oxide material and the catalyst metal material.

6. The gas detection method according to claim 1, wherein the metal oxide is a sintered body including the metal oxide material and the catalyst metal material.

7. The gas detection method according to claim 6, wherein the adsorption layer has a thickness of up to 30 microns.

8. The gas detection method according to claim 1, wherein the second temperature range is from 290° C. to 500° C.

9. The gas detection method according to claim 8, wherein the reducing gas includes methyl salicylate.

10. A gas detection method, comprising:

heating a semiconductor sensor that includes an adsorption layer formed of a metal oxide including a metal oxide material including a tungsten oxide and a catalyst metal material including rhenium;

measuring a resistance value of these miconductor sensor in an air atmosphere in which a reducing gas is present;

determining, where sensitivity, that is a ratio of aresistance value of the semiconductor sensor in an air atmosphere in which the reducing gas is not present to the measured resistance value, in a first temperature range from 80° C. to 220° C. is less than in a second temperature range from 290° C. or greater, that the reducing gas contains a hydrocarbon substance emitted from a plant or an animal.

11. An information processing apparatus, comprising:

an acquisition unit that acquires a resistance value of a metal oxide semiconductor sensor in an air atmosphere in which a reducing gas is present; and adetermination unit that determines, where the acquired resistance value in a first temperature range from 80° C. to 220° C. is higher than in a second temperature range from 290° C. or greater with reference to the resistance value of the semiconductor sensor in an air atmosphere in which the reducing gas is not present, that the reducing gas contains a hydrocarbon substance emitted from a plant or an animal, wherein the metal oxide semiconductor sensor includes an adsorption layer formed of a metal oxide including a metal oxide material including a tungsten oxide and a catalyst metal material including rhenium.

12. The gas detection method according to claim 11, wherein the metal oxide is a sintered body including the metal oxide material and the catalyst metal material.

13. The gas detection method according to claim 12, wherein the adsorption layer has a thickness of up to 30 microns.

14. An information processing apparatus, comprising:

an acquisition unit that acquires a resistance value of a metal oxide semiconductor sensor in an air atmosphere in which a reducing gas is present; and a determination unit that determines, where sensitivity, that is a ratio of a resistance value of the semiconductor sensor in an air atmosphere in which the reducing gas is not present to the acquired resistance value, in a first temperature range from 80° C. to 220° Cis less than in a second temperature range from 290° C. or greater, that the reducing gas contains a hydrocarbon substance emitted from a plant or an animal, wherein the metal oxide semiconductor sensor includes an adsorption layer formed of a metal oxide including a metal oxide material including a tungsten oxide and a catalyst metal material including rhenium.

15. A method of diagnosing a plant, comprising, in an area in which one or more plants to be tested are grown:

heating a semiconductor sensor that includes an adsorption layer formed of a metal oxide including a metal oxide material including a tungsten oxide and a catalyst metal material including rhenium; measuring a resistance value of the semiconductor sensor in an air atmosphere in which a reducing gas is present; determining, where sensitivity, that is a ratio of aresistance value of the semiconductor sensor in an air atmosphere in which the reducing gas is not present to the measured resistance value, in a first temperature range from 80° C. to 220° C. is less than in a second temperature range from 290° C. or greater, that the reducing gas contains a hydrocarbon substance emitted from a plant; and diagnosing a state of the plants in the area on a basis of detection information of a hydrocarbon substance emitted from the plants.

16. A method of diagnosing a plant, comprising, in an area in which one or more plants to be tested are grown:

heating a semiconductor sensor that includes an adsorption layer formed of a metal oxide including a metal oxide material including a tungsten oxide and a catalyst metal material including rhenium; measuring a resistance value of the semiconductor sensor in an air atmosphere in which a reducing gas is present;

determining, where sensitivity, that isaratio of aresistance value of the semiconductor sensor in an air atmosphere in which the reducing gas is not present to the measured resistance value, in a first temperature range from 80° C. to 220° C. is less than in a second temperature range from 290° C or greater, that the reducing gas contains a hydrocarbon substance emitted from plants; and diagnosing a state of the plants in the area on a basis of detection information of a hydrocarbon substance emitted from the plants.

17. A plant diagnosing apparatus, comprising, in an area in which one or more plants to be tested are grown:

an acquisition unit that acquires a resistance value of a metal oxide semiconductor sensor in an air atmosphere in which a reducing gas is present;

a determination unit that determines, where sensitivity, that is a ratio of a resistance value of the semiconductor sensor in an air atmosphere in which the reducing gas is not present to the acquired resistance value, in a first temperature range from 80° C. to 220° C. is less than in a second temperature range from 290° C. or greater, the reducing gas contains a hydrocarbon substance emitted from plants; and a diagnosis unit that diagnoses a state of the plants in the area on a basis of detection information of a hydrocarbon substance emitted from the plants obtained by the determination unit, wherein the metal oxide semiconductor sensor includes an adsorption layer formed of a metal oxide including a metal oxide material including a tungsten oxide and a catalyst metal material including rhenium.

18. A plant diagnosing apparatus, comprising, in an area in which one or more plants to be tested are grown;

an acquisition unit that acquires a resistance value of a metal oxide semiconductor sensor in an air atmosphere in which a reducing gas is present;

adetermination unit that determines, where the acquired resistance value in a first temperature range from 80° C. to 220° C. is higher than in a second temperature range from 290° or greater with reference to the resistance value of the semiconductor sensor in an air atmosphere in which the reducing gas is not present, that the reducing gas contains a hydrocarbon substance emitted from a plant; and a diagnosis unit that diagnoses a state of the plants in the area on a basis of detection information of a hydrocarbon substance emitted from the plants obtained by the determination unit, wherein the metal oxide semiconductor sensor includes an adsorption layer formed of a metal oxide including a metal oxide material including a tungsten oxide and a catalyst metal material including rhenium.

* * * * *